United States Patent
Hayes

(10) Patent No.: US 8,344,679 B2
(45) Date of Patent: Jan. 1, 2013

(54) METHOD AND APPARATUS TO MAINTAIN MOTION CONTROL DURING MANUAL PATIENT POSITIONING

(75) Inventor: John Hayes, Macedonia, OH (US)

(73) Assignee: Koninklijke PHilips Electronics N.V., Eindhoven (NL)

( * ) Notice: Subject to any disclaimer, the term of this patent is extended or adjusted under 35 U.S.C. 154(b) by 649 days.

(21) Appl. No.: 12/535,725

(22) Filed: Aug. 5, 2009

(65) Prior Publication Data

US 2010/0037394 A1    Feb. 18, 2010

Related U.S. Application Data

(60) Provisional application No. 61/089,060, filed on Aug. 15, 2008.

(51) Int. Cl.
A47B 13/00    (2006.01)

(52) U.S. Cl. .................. 318/626; 318/625; 318/628

(58) Field of Classification Search .............. 5/600–601, 5/613; 328/20; 382/132; 378/208–209; 318/625–628
See application file for complete search history.

(56) References Cited

U.S. PATENT DOCUMENTS

| | | | |
|---|---|---|---|
| 4,131,802 A * | 12/1978 | Braden et al. ................. | 378/20 |
| 5,825,843 A | 10/1998 | Kobayashi | |
| 6,776,527 B1 | 8/2004 | Tybinkowski et al. | |
| 7,293,308 B2 | 11/2007 | Everett et al. | |

* cited by examiner

*Primary Examiner* — Fredrick Conley

(57) ABSTRACT

A method and apparatus are provided to maintain motion control during manual positioning of a patient table. The method and apparatus of the present application control the amount of resistance to manual motion of the patient table without using switches to control the amount of assistance provided during manual positioning. The amount of resistance to manual motion may vary as a function of the velocity and position of the patient table. Further, the resistance to initial manual movement of the patient table may be reduced.

16 Claims, 3 Drawing Sheets

METHOD AND APPARATUS TO MAINTAIN MOTION CONTROL DURING MANUAL PATIENT POSITIONING

CROSS REFERENCE TO RELATED APPLICATIONS

This application claims the benefit of U.S. provisional application Ser. No. 61/089,060 filed Aug. 15, 2008, which is incorporated herein by reference.

DESCRIPTION

The present application relates generally to the imaging arts and more particularly to an apparatus and method to maintain motion control during manual patient positioning. It finds use in various types of imaging systems in which a patient must be positioned within or relative to an imaging device, such as for example, Magnetic Resonance ("MR"), Computed Tomography ("CT"), Positron Emission Tomography ("PET"), and Single Photon Emission Computed Tomography ("SPECT").

Patient tables may include linear or rotary positioning systems. Most common are linear positioning systems in which the patient table moves in and out of the imaging device. Rotary positioning systems rotate the patient table between imaging devices, such as for example, an MR and a PET imaging device. Rotary positioning systems may be combined with linear positioning systems. Patient positioning systems generally include a servo motor that moves the patient table. The encoder of the servo motor monitors the position and velocity of the motor shaft and sends this information to a control system. The control system controls the current applied to the servo motor so as to accurately position the patient table relative to the imaging device. The positioning system may include logic that allows for automatic positioning of the patient table.

Patient positioning systems generally include a means to manually position the patient table. One method of manually positioning the patient table includes the use of switches that control the servo motor. By operating the switches, a human operator can move the patient table via the servo motor. This method is inefficient, slow, and does not allow for quick removal of the patient table from the imaging device.

Another method of manual positioning generally includes a means to disconnect the servo motor from the mechanics of the patient table. Such disconnection can be mechanically achieved, for example, with a clutch or brake release mechanism. It may also be achieved electrically, by cutting off the power supply to the servo motor. Once the servo motor is disconnected from the patient table, the table may be moved manually by a human operator pushing or pulling the table with resistance provided only by the mechanics of the table. However, with the servo motor disconnected, the encoder is unable to send signals to the control system reporting the position and velocity of the motor shaft and thus of the patient table. This reduces the efficiency of the system. For example, the electromechanical limits of motion of the patient table may be breached resulting in a fault condition which could, for example, cause an emergency stop condition to be triggered. Further, patient discomfort may result from the patient table running into a mechanical limit.

According to one aspect of the present invention, a method and apparatus are provided to maintain motion control of the patient table during manual patient positioning.

According to a particular aspect of the present invention, a method is provided to control the amount of assistance or resistance to manual motion of the patient table (e.g., linear or rotary motion) while leaving the servo motor electrically enabled and mechanically connected to the mechanics of the patient table. The amount of assistance or resistance to manual motion provided by the servo motor may vary based on the velocity and the position of the patient table. For example, the servo motor may assist manual motion as the operator moves the patient table within predetermined velocity and position limits. Further, the servo motor may resist manual motion as the patient table approaches and/or exceeds the velocity and position limits. Traditional methods of manual patient table positioning provide no such control to the amount of assistance or resistance to manual motion.

According to another aspect of the present invention, an apparatus is provided to control the amount of assistance or resistance to manual motion of the patient table. The apparatus may include a switch to enable manual positioning of the patient table and logic that automatically controls the amount of assistance or resistance to manual motion based on the velocity and position of the patient table. The apparatus does not, however, need additional switches to provide assistance or resistance during manual positioning of the patient table.

This method is more efficient than only allowing the servo motor to drive the patient table in and out of the imaging device. Further, the servo motor remains electrically enabled and mechanically connected to the mechanics of the patient table such that the position and velocity of the patient table are known during manual positioning. As such, the patient table is prohibited from exceeding velocity and position limits by providing increased resistance as the patient table approaches and/or exceeds these limits.

Numerous additional advantages and benefits will become apparent to those of ordinary skill in the art upon reading the following detailed description of preferred embodiments. The invention may take form in various components and arrangements of components, and in various process operations and arrangements of process operations.

The drawings are only for the purpose of illustrating preferred embodiments and are not to be construed as limiting the invention.

The present application is directed generally to a method and apparatus to maintain motion control of the patient table during manual patient positioning. One example of such an apparatus is the representative patient positioning system 100 shown in FIG. 1. The patient positioning method and apparatus disclosed herein have application with various types of imaging systems, which may differ from FIG. 1 in many respects.

Figure 1:
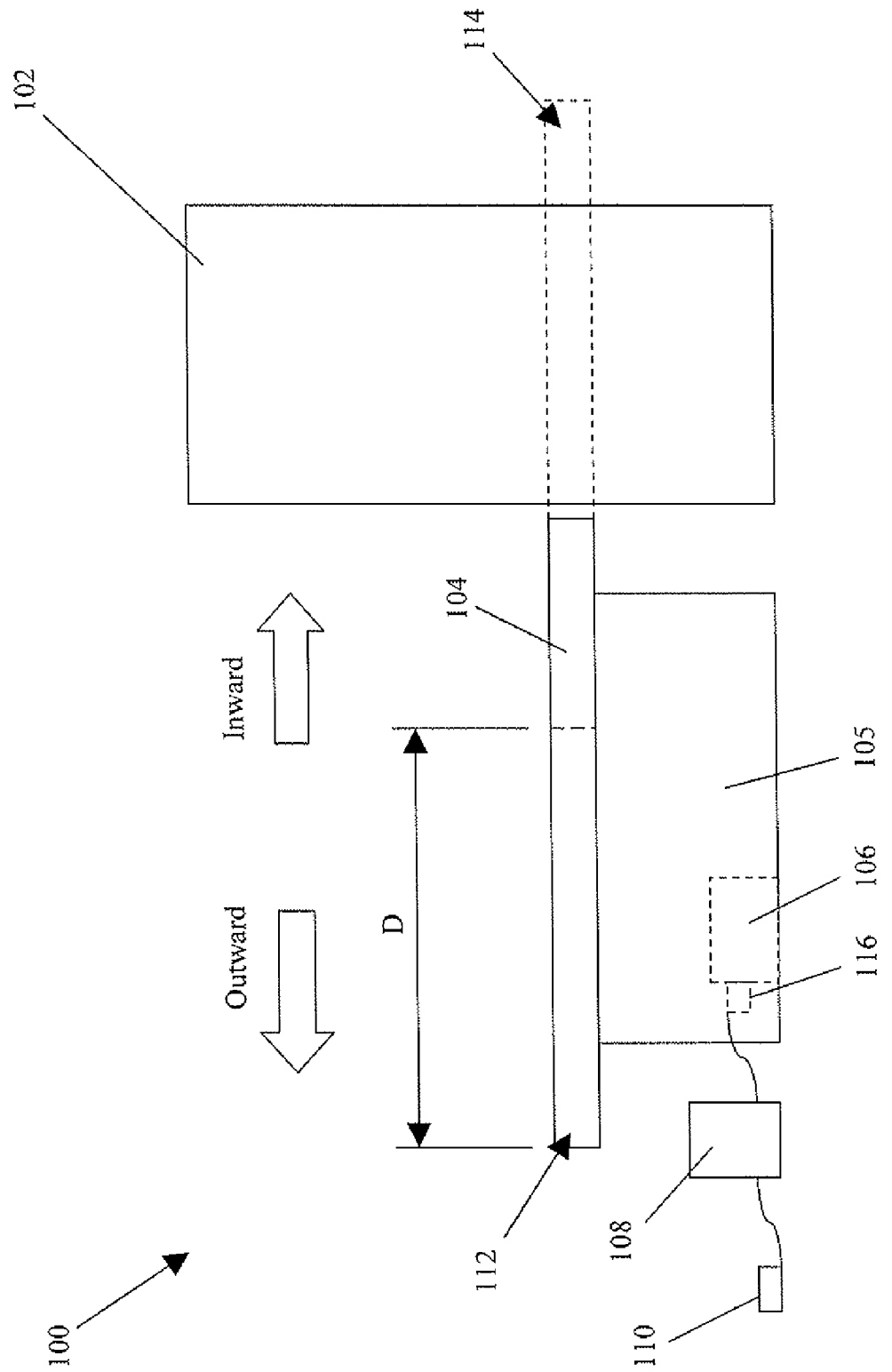
FIG. 1 is a schematic representation of a patient positioning system according to an embodiment of the invention.

As illustrated in FIG. 1, the patient positioning system 100 includes an imaging device 102, a patient table 104, a servo motor 106, a control system 108, and a switch 110. The patient table 104 is slidably mounted on top of a base 105, between a loading position 112 and an imaging position 114. The patient table 104 is shown in solid lines outside the imaging device 102 in the patient loading position 112. Further, the patient table 104 is shown in broken lines within the imaging device 102 in the patient imaging position 114. The patient table 104 moves in and out of the imaging device 102 between the patient loading position 112 and the patient imaging position 114, as illustrated by arrows. The patient positioning system 100 includes limits on the inward and outward movement of the patient table 104. The range of motion or travel of the patient table 104 between these limits is represented by a distance D, which may be for example about 2000 mm.

As shown, the patient table 104 is driven in and out of the imaging device 102 by a servo motor 106. For example, the shaft of the servo motor 106 may be connected to the table by a series of gears or a drive belt (not shown). As such, the bidirectional rotation of the servo motor 106 shaft will in turn move the patient table in and out of the imaging device 102. An encoder 116 of the servo motor 106 monitors the direction (e.g., clockwise or counterclockwise), velocity (e.g., revolution per minute), and position (e.g., degrees) of the servo motor shaft and sends this information to a control system 108.

The control system 108 of the patient positioning system 100 controls the current applied to the servo motor 106 to accurately position the patient table 104 relative to the imaging device 102. The information sent by the encoder 116 is utilized by the control system 108 to calculate the position, velocity, and direction of the patient table 104. Further, logic may be used to automatically move and position the patient table 104 at various predetermined locations, such as for example, the patient loading position 112 and patient imaging position 114. The switch 110 of the patient positioning system 100 allows the operator to enable manual positioning of the patient table 104. The switch may be any suitable switch known in the art, such as for example, a foot switch, a button, or a toggle switch.

Once the operator enables manual positioning of the patient table 104 via the switch 110, the control system 108 enters into a hold mode. In hold mode, the control system 108 alternates the current supplied to the servo motor 106 back and forth at an amount just below what is required to move the table 104, such as for example, 2.5% of a maximum ("max") power. As such, the servo motor 106 holds the patient table 104 in place by alternating between driving the table into and out of the imaging device 102. Because the current is just below what is required to move the patient table 104, the alternating forces tend to cancel each other so that the table 104 does not move or just slightly rocks back and forth. The amount of current required to move the patient table 104 may vary depending on several factors, including but not limited to, the weight of the table 104, resistance due to the mechanics of the table 104, and various patient parameters (e.g., weight, height, and age). As such, the percentage of max power required to move the patient table 104 may require calibration.

With the control system 108 in hold mode, a human operator can manually move the table 104 by pushing or pulling on the table 104 with his or her hands. This manually applied force combines with the alternating force provided by the servo motor 106 (with the control system 108 in hold mode) to move the patient table 104. As such, the force required by the operator to initially move the patient table 104 and overcome the mechanical friction and the inertia of the components in the system, or "stiction," is reduced due to the assistance provided by the servo motor 106 in the direction of travel. As the human operator moves the patient table 104 beyond an adjustable minimum threshold, such as for example 10-20 mm, and/or as the velocity of the table increases above an adjustable minimum threshold, such as for example slightly above 0 mm/s, the control system 108 enters an assist mode.

With the control system 108 in assist mode, the servo motor 106 applies additional force on the table 104 in the direction of travel. The percentage of power supplied to the servo motor 106 in assist mode may vary as a function of the velocity of the patient table 104. For example, as the velocity of the patient table 104 increases, the amount of assistance provided by the servo motor 106 may be reduced due to the inertia of the moving table. If the operator reduces the force he or she applies to the patient table 104 and the velocity of the table drops below an adjustable minimum threshold, such as for example slightly above 0 mm/s, the amount of assistance provided by the servo motor 106 will be reduced or eliminated, gently stopping the table. Similarly, in certain embodiments, the amount of assistance provided by the servo motor 106 will be reduced or eliminated if the patient table 104 reaches a maximum velocity threshold, such as for example 170 mm/s.

The percentage of power supplied to the servo motor 106 may also vary as a function of the position of the patient table 104 when the control system 108 is in assist mode. For example, the amount of assistance provided by the servo motor 106 may be reduced if the patient table 104 nears a position limit, such as for example within 50 mm of the position limit (i.e., a soft stop). Further, in certain embodiments, the servo motor 106 may increase the resistance to motion beyond the resistance inherent in the mechanics of the patient table 104 by applying a force on the table in a direction opposite the direction of travel, such as for example, when the table nears or reaches a position limit (i.e., a position lock).

Figure 3:
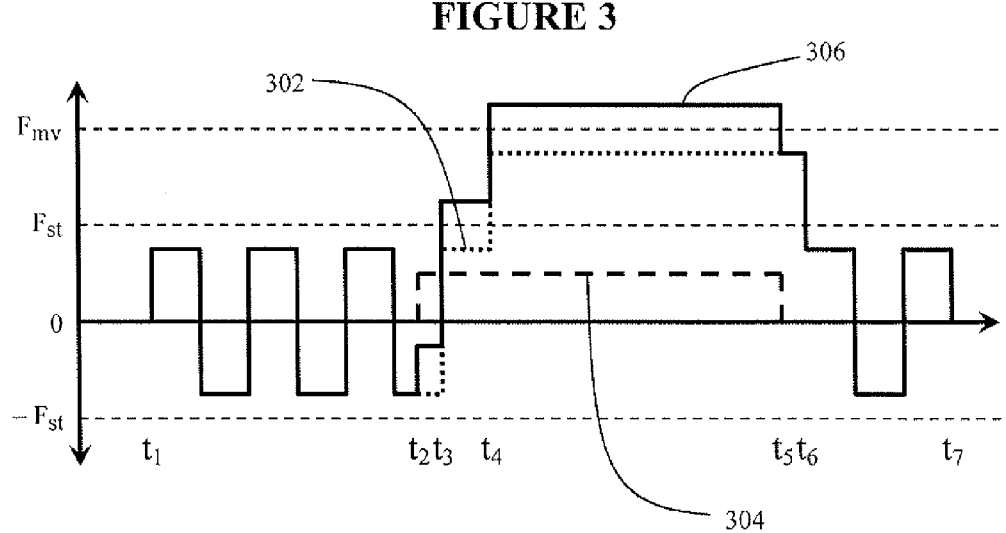
FIG. 3 illustrates the forces applied as a patient table is manually positioned over a period of time according to an embodiment of the invention.

FIG. 3 illustrates the forces applied as the table 104 is manually positioned over a period of time. The force $F_{st}$ is the approximate force necessary to move the table 104 by overcoming the "stiction." The force $F_{mv}$ is the force necessary to sustain table 104 movement at a constant velocity. The dotted line 302 represents the force being applied by the servo motor 106, as operated by the current supplied by the control system 108. The dashed line 304 represents the external pushing or pulling force being applied by an operator to the table 104. The solid line 306 represents the sum of those two forces 302 and 304. Thus, as described further below, in portions of FIG. 3 where only one force 302 or 304 is being applied, the solid line 306 represents only that force 302 or 304.

Figure 4:
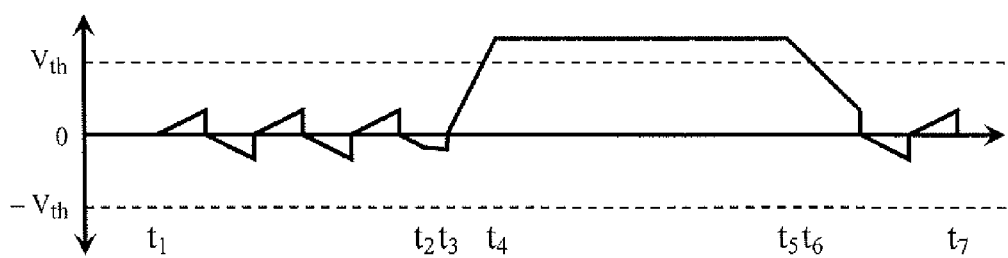
FIG. 4 illustrates the table velocity resulting from the forces applied, as shown in FIG. 3, as the table is manually positioned over a period of time.

FIG. 4 illustrates the table velocity resulting from the forces applied, as shown in FIG. 3, as the table 104 is manually positioned over a period of time. The velocity $V_{th}$ represents the minimum velocity threshold for the control system 108 to enter assist mode.

At time $t_1$, the switch 110 is engaged to permit manual positioning of the table 104. When the switch 110 is engaged, the control system 108 enters hold mode. The control system 108 thus provides an alternating current to the servo motor 106, resulting in an alternating force being applied. As shown in FIG. 3, the magnitude of the alternating force is just slightly less than $F_{st}$, the approximate force necessary to overcome the "stiction" of the table 104. Thus, as the servo motor force alternates in hold mode, there may be some small resulting movement of the table 104 as illustrated in FIG. 4, or there may be no movement at all. During this initial hold period, the operator is not pushing or pulling on the table 104, so the total force 306 is equal to the force 302 being applied by the servo motor 106.

At time $t_2$, the operator applies an external force 304 by pushing or pulling on the table 104. In this example, the external force 304 is approximately half of the "stiction"

force $F_{st}$. At time $t_3$, the alternating force 302 applied by the servo motor 106 aligns in the same direction as the operator force 304, resulting in a combined force 306 which exceeds the "stiction" force $F_{st}$. As a result, as shown in FIG. 4, the velocity of the table 104 continues to increase in the direction of the force 304 applied by the operator. Thus, in this way, the operator need not provide the entire force necessary to overcome the "stiction" force $F_{st}$, as the alternating servo motor force 302 provides some assistance even in hold mode.

At time $t_4$, the increasing table velocity reaches the minimum velocity threshold $V_{th}$ for the control system 108 to switch from hold mode to assist mode. So, at time $t_4$, the control system 108 operates the servo motor 106 to stop applying an alternating force 302, instead applying a constant assist force 302 in the direction of table travel. In the illustrated example, that assist force 302 is a small amount less than $F_{mv}$, the force necessary to sustain table 104 movement at a constant velocity. Thus the assist force 302 combined with the external force 304 provided by the operator result in a total force 306 which exceeds the force $F_{mv}$, and the table 104 moves in the direction of the external force 304.

At time $t_5$, the external force 304 applied by the operator is removed, so that the total force 306 is equal to the servo motor force 304. Because that force is less than $F_{mv}$, the velocity of the table 104 begins to decrease. The control system 108 nonetheless maintains the servo motor 106 in assist mode, applying a constant force 302, until the time $t_6$ when the velocity of the table 104 drops below the minimum velocity threshold $V_{th}$. At that time $t_6$, the control system 108 enters hold mode and so returns to applying an alternating force 302. At time $t_7$, the switch 110 is released, returning the system 100 to a non-manual operating mode.

Although the patient positioning system 100 shown in FIG. 1 is linear, a similar method and apparatus may be used to control the amount of resistance to manual motion of a patient table in a rotary system. However, in a rotary system, the patient table is rotated by the servo motor instead of being driven linearly in and out of the imaging device. As such, the velocity and position limits of the patient table in the rotary system are angular. In yet additional embodiments, a positioning system 100 may be a combined rotary and linear system.

Similar to the linear patient positioning system 100, in a rotary system, the operator manually moves the table by pushing or pulling the table with his or her hands to rotate the table. This manually applied force can cause a control system to change from a hold mode to an assist mode, as described above. The percentage of power supplied to the servo motor may also vary as a function of the velocity and position of the patient table, as described above.

The aforementioned functions, such as for example, controlling the amount of assistance or resistance provided by the servo motor of the patient positioning systems, can be performed as software logic. As such, the operator need not manipulate switches that control whether the system provides assistance during manual positioning of the patient table. "Logic," as used herein, includes but is not limited to hardware, firmware, software and/or combinations of each to perform a function(s) or an action(s), and/or to cause a function or action from another component. For example, based on a desired application or needs, logic may include a software controlled microprocessor, discrete logic such as an application specific integrated circuit (ASIC), or other programmed logic device. Logic may also be fully embodied as software.

"Software," as used herein, includes but is not limited to one or more computer readable and/or executable instructions that cause a computer or other electronic device to perform functions, actions, and/or behave in a desired manner. The instructions may be embodied in various forms such as routines, algorithms, modules or programs including separate applications or code from dynamically linked libraries. Software may also be implemented in various forms such as a stand-alone program, a function call, a servlet, an applet, instructions stored in a memory, part of an operating system or other type of executable instructions. It will be appreciated by one of ordinary skill in the art that the form of software is dependent on, for example, requirements of a desired application, the environment it runs on, and/or the desires of a designer/programmer or the like.

The systems and methods described herein can be implemented on a variety of platforms including, for example, networked control systems and stand-alone control systems. Additionally, the logic, databases or tables shown and described herein preferably reside in or on a computer readable medium, such as a component of the control system 108. Examples of different computer readable media include Flash Memory, Read-Only Memory (ROM), Random-Access Memory (RAM), programmable read-only memory (PROM), electrically programmable read-only memory (EPROM), electrically erasable programmable read-only memory (EEPROM), magnetic disk or tape, optically readable mediums including CD-ROM and DVD-ROM, and others. Still further, the processes and logic described herein can be merged into one large process flow or divided into many sub-process flows. The order in which the process flows herein have been described is not critical and can be rearranged while still accomplishing the same results. Indeed, the process flows described herein may be rearranged, consolidated, and/or re-organized in their implementation as warranted or desired.

Figure 2:
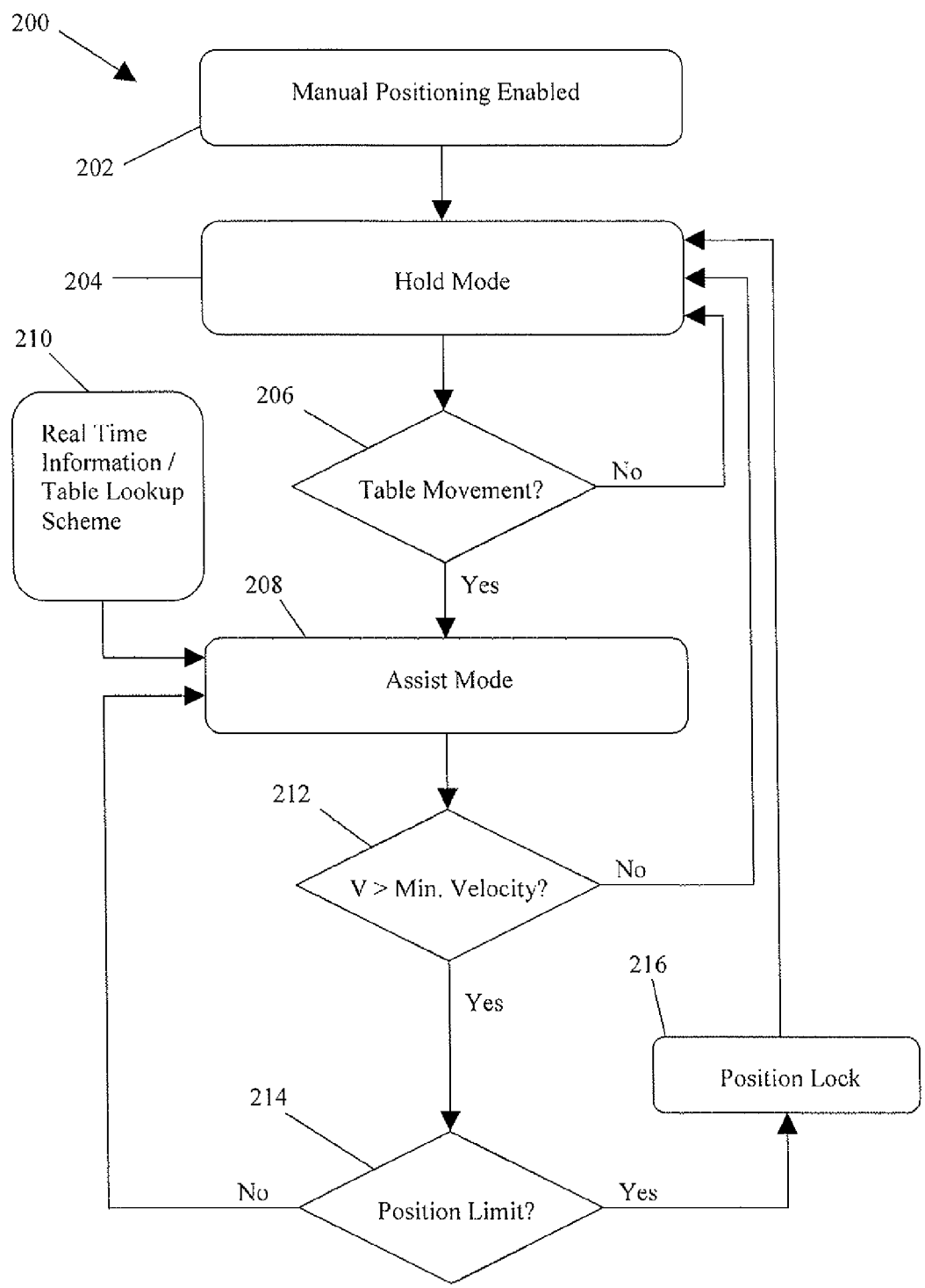
FIG. 2 illustrates a process to maintain motion control during manual patient positioning according to an embodiment of the invention.

For example, such a process 200 is shown in FIG. 2. Initially, as shown in FIG. 2, the operator of the patient positioning system manipulates a switch 110 to enable manual positioning of the patient table, step 202. Once manual positioning is enabled, the software logic will enter a hold, or float, mode, step 204, as described above.

While in hold mode, the software logic monitors whether the patient table begins to move or rotate beyond an adjustable minimum position threshold and/or at a velocity equal to or greater than an adjustable minimum velocity threshold, step 206. The minimum distance threshold and minimum velocity threshold are adjustable and may be any suitable minimum distance or velocity. If the software logic does not sense a sufficient movement, the system will remain in hold mode. However, once the operator pushes or pulls the patient table and the table begins to move beyond the minimum distance threshold and/or at a velocity greater than the minimum velocity threshold, the software logic will enter an assist mode, step 208, as described above.

In some embodiments, the amount of assistance provided by the servo motor while in assist mode will not vary. For example, the amount of current supplied to the servo motor may be set to a selectable percentage of max power, such as for example, 4% of max power. The servo motor will provide assistance at this percentage of max power until the patient table approaches or exceeds velocity and position limits. The set percentage of max power may depend on multiple factors, including but not limited to, the amount of resistance inherent in the mechanics of the patient table, the weight of the table, and various patient parameters (e.g., weight, height, and age).

In other embodiments, the amount of assistance provided by the servo motor while in assist mode may vary. For example, the amount of current supplied to the servo motor may vary based on the velocity and/or position of the patient table. As the velocity of the patient table approaches a maximum threshold, such as for example, 170 mm/s (linear) or 9 degrees/s (rotary), the percentage of max power may decrease as a function of velocity. For example, the assistance my decrease from 100% of max power to approximately 0% of max power, such that the velocity of the table stays at or below the maximum velocity threshold. Similarly, as the patient table approaches a position limit, such as for example, 0 mm and 2000 mm (linear) or 0 degrees and 180 degrees (rotary), the percentage of max power may decrease as a function of distance to the limit, such as for example, from 100% of max power to approximately 0% of max power, to gently stop the patient table (i.e., a soft stop).

The amount of assistance provided by the servo motor as a function of velocity and position may be derived using various sources, step 210. For example, the assistance may vary based on real time calculations using information provided by the encoder or other source. It may also vary based on a table lookup scheme or other stored memory, or from a combination of real time calculations and stored memory. Further, the amount of assistance provided by the servo motor may be derived using various patient parameters, such as for example, the patient's weight, height, and age.

While in assist mode, the software logic monitors whether the velocity of the patient table falls below an adjustable minimum threshold, step 212. If the velocity of the patient table is above this threshold, the system will remain in assist mode. However, if the velocity of the patient table dips below the minimum threshold, the system will return to hold mode. As stated, the minimum threshold is adjustable and may be any suitable velocity. Further, the minimum threshold velocity may depend on multiple factors, including but not limited to, the amount of resistance inherent in the mechanics of the patient table, the weight of the table, and various patient parameters (e.g., weight, height, and age).

Similarly, while in assist mode, the software logic monitors whether the position of the patient table falls within adjustable position limits, step 214. If the position of the patient table is within the position limits, the system will remain in assist mode. However, if the position of the patient table meets or perhaps closely approaches a position limit, the system will return to hold mode. In some embodiments, the servo motor may resist any motion beyond a position limit by applying a force on the patient table in a direction opposite the direction of travel (i.e., a position lock), step 216.

As a representative example, assume the distance D in FIG. 1 is 2000 mm, and the table 104 begins at D=1000 mm with the control system 108 in hold mode. The operator then pushes the table 104 into the imaging device 102. The control system 108 detects that movement and enters assist mode to help move the table 104. However, when the table 104 approaches the extreme D=2000 mm limit, such as for example when D=1950 mm, the control system 108 will eliminate any assistance and return to hold mode. In this way the table 104 may be gently stopped before it reaches the mechanical limit D=2000 mm. Further, if the operator attempts to push the table 104 beyond the mechanical limit D=2000 mm, the control system 108 will enter a position lock mode. In position lock mode, the servo motor will resist any motion beyond mechanical limit D=2000 mm by applying a force on the patient table in the opposite direction.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof. The invention may take form in various components and arrangements of components, and in various steps and arrangements of steps. The drawings are only for purposes of illustrating the preferred embodiments and are not to be construed as limiting the invention.

Having thus described the preferred embodiments, the invention is now claimed to be:

1. An apparatus to control motion of a patient table during manual positioning, the apparatus comprising:
   a servo motor assisting a manual movement of the patient table by providing an assist force to reduce resistance to the manual movement, wherein the assisted manual movement is caused by a manual force which is different from the servo motor; and
   a control system comprising a computer readable medium including logic for controlling the servo motor;
   wherein the logic provides for reduction of the assist force provided by the servo motor as the patient table approaches at least one of an adjustable velocity limit and an adjustable position limit.

2. The apparatus of claim 1, further comprising a switch that disables the manual movement of the patient table in a first position, and enables the manual movement of the patient table in a second position.

3. The apparatus of claim 2, wherein moving the switch to the second position causes the control system to enter a hold mode in which the servo motor provides an alternating force to the patient table at an amount less than an amount of force required to move the patient table when the patient table is not being manually positioned.

4. The apparatus of claim 3, wherein the amount of the alternating force is determined based on at least a weight of the table and one or more patient parameters.

5. The apparatus of claim 3, wherein the computer readable medium of the control system comprises logic to monitor at least one of the position and the velocity of the patient table when the control system is in the hold mode, and the control system enters an assist mode to provide the assist force if the monitored position or the monitored velocity increases above a minimum threshold.

6. The apparatus of claim 5, wherein the computer readable medium of the control system comprises logic to monitor at least one of the position and the velocity of the patient table when the control system is in the assist mode, and the control system returns to the hold mode if the patient table approaches at least one of the adjustable velocity limit and the adjustable position limit.

7. The apparatus of claim 5, wherein the servo motor provides a resist force to increase resistance to the manual movement of the patient table as the patient table approaches or meets an adjustable position limit.

8. The apparatus of claim 1, further comprising a servo motor encoder to monitor the position and the velocity of the patient table, and provide the position and velocity information to the control system.

9. The apparatus of claim 1, further comprising an imaging device into which the patient table may be inserted.

10. The apparatus of claim 9, wherein the imaging device comprises at least one of a CT imaging system and a PET imaging system.

11. The apparatus of claim 1, wherein the manual movement is one of a linear movement and a rotary movement.

12. The apparatus of claim 1, wherein the assist force provided by the servo motor is eliminated when the patient table meets at least one of the adjustable velocity limit and the adjustable position limit.

13. The apparatus of claim 1, wherein the servo motor provides a resist force to increase resistance to the manual movement of the patient table as the patient table approaches or meets the adjustable position limit.

14. The apparatus of claim 1, wherein the amount of assist force provided by the servo motor varies depending on at least one of the position and the velocity of the patient table.

15. The apparatus of claim 1, wherein the amount of assist force provided by the servo motor is determined using at least one of real time information, a table lookup scheme, and patient parameters.

16. The apparatus of claim 1, wherein the servo motor provides an alternating force to the patient table at an amount less than an amount of force required to move the patient table when the patient table is not being manually positioned.

* * * * *